United States Patent
Opfer et al.

(10) Patent No.: US 10,311,971 B2
(45) Date of Patent: Jun. 4, 2019

(54) PET/CT BASED MONITORING SYSTEM SUPPORTED BY A CLINICAL GUIDELINE NAVIGATOR

(75) Inventors: Roland Johannes Opfer, Hamburg (DE); Lilla Boroczky, Mount Kisco, NY (US); Ingwer Curt Carlsen, Hamburg (DE); Pradyumna Dutta, Bedford Corners, NY (US); Steffen Renisch, Hamburg (DE); Joerg Sabczynski, Norderstedt (DE); Paola Karina Tulipano, Englewood, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 39 days.

(21) Appl. No.: 13/260,533

(22) PCT Filed: Feb. 11, 2010

(86) PCT No.: PCT/IB2010/050638
§ 371 (c)(1),
(2), (4) Date: Dec. 9, 2011

(87) PCT Pub. No.: WO2010/109350
PCT Pub. Date: Sep. 30, 2010

(65) Prior Publication Data
US 2012/0123801 A1 May 17, 2012

Related U.S. Application Data

(60) Provisional application No. 61/163,597, filed on Mar. 26, 2009.

(51) Int. Cl.
*G16H 30/20* (2018.01)
*G16H 20/40* (2018.01)
(Continued)

(52) U.S. Cl.
CPC ............. *G16H 30/20* (2018.01); *A61B 6/037* (2013.01); *G06F 19/321* (2013.01); *G06Q 50/24* (2013.01);
(Continued)

(58) Field of Classification Search
CPC ........ G16H 30/20; G16H 20/40; G16H 10/60; G06Q 50/24; A61B 6/037; G06F 19/321
(Continued)

(56) References Cited

U.S. PATENT DOCUMENTS 5,732,697 A 3/1998 Zhang et al.
6,904,161 B1 * 6/2005 Becker et al. ................ 382/128
(Continued)

FOREIGN PATENT DOCUMENTS

| EP | 1454585 A1 | 8/2004 |
|---|---|---|
| JP | 2007287027 A | 11/2007 |
| WO | 2005001740 A2 | 1/2005 |

OTHER PUBLICATIONS

"Plan." The American Heritage Dictionary of the English Language. Eds. The Editors of the American Heritage Dictionaries, The Editors of the American Heritage Dictionaries, and The Editors of the American Heritage Dictionaries. Boston: Houghton Mifflin, 2011. Credo Reference. Web. Apr. 9, 2015.*
(Continued)

*Primary Examiner* — Jonathan Durant

(57) ABSTRACT

An oncology monitoring system comprises: an image analysis module (42, 44) configured to perform an oncological monitoring operation based on images of a subject, for example acquired by positron emission tomography (PET) and computed tomography (CT); and a clinical guideline support module (10). The clinical guideline support module is configured to: display a graphical flow diagram (GFD) of a clinical therapy protocol for treating the subject compris-
(Continued)

Figure 1:
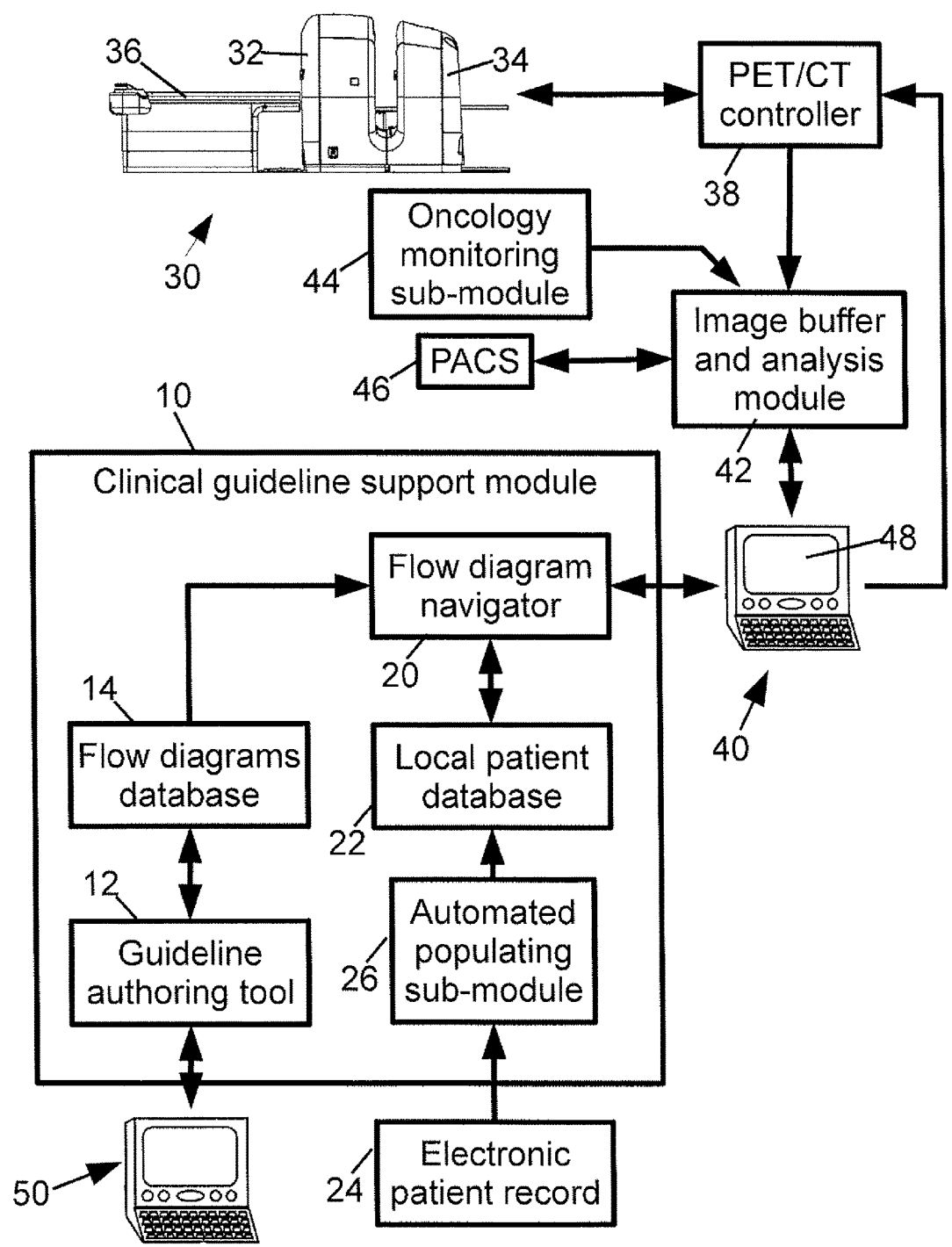

ing graphical blocks (B0, B1, B2, B3, B4, B5, B21, B211, B22, B221, B222, B223, B23, B231, B232) representing therapeutic or monitoring operations of the clinical therapy protocol including at least one monitoring operation performed by the image analysis module; annotate a graphical block of the graphical flow diagram with subject-specific information pertaining to a therapeutic or monitoring operation represented by the graphical block; and display an annotation (POP) of a graphical block (B211) responsive to selection of the graphical block by a user.

10 Claims, 2 Drawing Sheets

(51) Int. Cl.
    *A61B 6/03*         (2006.01)
    *G06F 19/00*       (2018.01)
    *G06Q 50/24*       (2012.01)
    *G16H 10/60*       (2018.01)
    *A61B 6/00*        (2006.01)

(52) U.S. Cl.
    CPC ............. *G16H 10/60* (2018.01); *G16H 20/40* (2018.01); *A61B 6/508* (2013.01)

(58) Field of Classification Search
    USPC ........................................................ 705/2, 3
    See application file for complete search history.

(56) References Cited

U.S. PATENT DOCUMENTS

| | | | |
|---|---|---|---|
| 7,603,182 | B2 | 10/2009 | Sano et al. |
| 7,640,051 | B2 | 12/2009 | Krishnan et al. |
| 7,949,166 | B2 | 5/2011 | Moriya et al. |
| 8,010,184 | B2 | 8/2011 | Avila et al. |
| 2004/0008876 | A1 | 1/2004 | Lure et al. |
| 2004/0254465 | A1* | 12/2004 | Sano et al. ................... 600/443 |
| 2005/0049497 | A1* | 3/2005 | Krishnan et al. ............ 600/437 |
| 2005/0160398 | A1* | 7/2005 | Bjornson et al. ............ 717/104 |
| 2006/0274928 | A1* | 12/2006 | Collins et al. ............... 382/132 |
| 2007/0101295 | A1 | 5/2007 | Ding et al. |
| 2007/0106633 | A1* | 5/2007 | Reiner ............................. 707/1 |
| 2007/0127793 | A1 | 6/2007 | Beckett et al. |
| 2007/0136095 | A1* | 6/2007 | Weinstein ....................... 705/2 |
| 2007/0167697 | A1 | 7/2007 | Avila et al. |
| 2009/0132580 | A1* | 5/2009 | James et al. .................. 707/102 |
| 2009/0287066 | A1* | 11/2009 | Meissner et al. ............. 600/300 |
| 2012/0123801 | A1 | 5/2012 | Opfer et al. |

OTHER PUBLICATIONS

"Protocol." The American Heritage Dictionary of the English Language. Eds. The Editors of the American Heritage Dictionaries, The Editors of the American Heritage Dictionaries, and The Editors of the American Heritage Dictionaries. Boston: Houghton Mifflin, 2011. Credo Reference. Web. Apr. 9, 2015.*

"Session." The American Heritage Dictionary of the English Language. Eds. The Editors of the American Heritage Dictionaries, The Editors of the American Heritage Dictionaries, and The Editors of the American Heritage Dictionaries. Boston: Houghton Mifflin, 2011. Credo Reference. Web. Apr. 9, 2015.*

Wikipedia:How to draw a diagram with Dia. Archived Nov. 27, 2007. Internet Archive Wayback Machine. Retrieved Apr. 8, 2015. <https://web.archive.org/web/20071127053131/http://en.wikipedia.org/wiki/Wikipedia:How_to_draw_a_diagram_with_Dia>.*

Dia (software). Archived Aug. 8, 2007. Internet Archive Wayback Machine. Retrieved Apr. 8, 2015. <https://web.archive.org/web/20070808100803/http://en.wikipedia.org/wiki/Dia_%28software%29>.*

The KOffice Project. Archived Oct. 20, 2007. Internet Archive Wayback Machine. Retrieved Apr. 8, 2015. <https://web.archive.org/web/20071020002323/http://www.koffice.org/kivio/>.*

Kivio: Powerful Flowchart Program for KDE. Archived Oct. 25, 2007. Internet Archive Wayback Machine. Retrieved Apr. 8, 2015. <https://web.archive.org/web/20071025045710/http://www.thekompany.com/projects/kivio/>.*

Kivio. Archived Aug. 8, 2007. Internet Archive Wayback Machine. Retrieved Apr. 8, 2015. <https://web.archive.org/web/20071103073840/http:en.wikipedia.org/wiki/Kivio>.*

Tessler, Franklin. "ConceptDraw V Professional 5.5." Macworld. Mar. 3, 2006. Web. Retrieved Apr. 9, 2015. <http://www.macworld.com/article/1049667/conceptdraw55.html>.*

By Delphine Rossille et al.; Entitled: "Modelling a Decision-Support System for Oncology Using Rule-Based and Case-Based Reasoning Methodologies"; Laboratoire d'Informatique Médicale, Université de Rennes 1, 2 avenue du Professeur Léon Bernard, 35043 Rennes Cedex, France Department of Systems and Computer Engineering, Carleton University, Ottawa, Canada • Centre Eugéne Marquis, Rennes, France Received Oct. 31, 2003; received in revised form Jun. 15, 2004; accepted Jun. 23, 2004; pp. 1-8.

By Wolfgang A. Weber et al.; Entitled: "Monitoring Cancer Treatment with PET/CT: Does It Make a Difference?"; 1Department of Molecular and Medical Pharmacology, University of California, Los Angeles, California; and 2Division of Medical Oncology and Therapeutics Research, City of Hope Comprehensive Cancer Center, Los Angeles, California; The Journal of Nuclear Medicine • vol. 48 • No. 1 (Suppl) • Jan. 2007; pp. 36S-44S.

By Didier Lardinois, M.D. et al.; Entitled: Staging of Non-Small-Cell Lung Cancer with Integrated Positron-Emission Tomography and Computed Tomography;Staging of Non-Small-Cell Lung Cancer with Integrated Positron-Emission Tom . . . Page 1 of 5.

Wiemker, R. "Automatic lesion tracking for a PET/CT based computer aided cancer therapy monitoring system", Medical Imaging 2008: Computer-Aided Iagnosis, (2008), vol. 6915, p. 691513.

* cited by examiner

PET/CT BASED MONITORING SYSTEM SUPPORTED BY A CLINICAL GUIDELINE NAVIGATOR

The following relates to the medical arts, clinical arts, medical imaging arts, and related arts.

Cancer treatment is typically a long-term process in which numerous clinical and diagnostic tools are marshaled to synergistically control, or ideally eliminate, the malignancy. In a typical cancer treatment timeline, the subject is initially diagnosed as having cancer, and baseline parameters such as weight, age, vital signs, blood cell counts, imaging of tumor, and so forth are obtained to assess the state of the patient. A series of therapies are then performed, which may include chemotherapy, brachytherapy, radiation therapy, or the like. Typically, these therapies are performed over an extended period of time and take the form of chemotherapy, brachytherapy, or radiation therapy sessions. At each session, the patient enters the hospital on an in-patient or out-patient basis, and undergoes a therapy treatment session. A recovery period follows typically between a few days and a few weeks. Additional diagnostics are sometimes performed during the recovery period, such as blood tests, tumor imaging, and so forth, in order to assess patient response to the treatment. This sequence is repeated for a number of chemotherapy, brachytherapy, or radiation therapy sessions. Afterward, extensive diagnostic tests are performed to assess the effect of the treatment. The overall therapy comprising several successive therapy sessions is performed in accordance with a clinical therapy protocol, which is usually embodied as a text-based document that is referenced by clinicians performing patient treatment operations.

As already noted, before and at selected points during the chemotherapy, brachytherapy, or radiation therapy, various diagnostic tests are performed to establish the patient baseline, to monitor patient response to the ongoing therapy treatment, and afterward to assess the effect of the completed therapy protocol. Early response assessment of cancer therapy can enable more effective and patient individualized cancer therapy. For example, the chemotherapy or radiation dosage, the time intervals between therapy sessions, the chemotherapy regimen, or other parameters can be adjusted based on the early response assessment.

Two techniques that have been used in response assessment include computed tomography (CT) and positron emission tomography (PET). CT and PET are complementary techniques in that CT tends to provide morphological information relating to the structure of a cancerous tumor or other malignancy, while PET tends to provide functional information relating to metabolic activity of the malignancy. For example, PET imaging using a fluoro-deoxy-glucose (FDG) radiopharmaceutical (FDG-PET) employed in combination with CT has been shown to improve response assessment. See, e.g., Weber et al., "Monitoring cancer treatment with PET/CT: Does it make a difference?", Journal of Nuclear Medicine, 48:36S-44S (2007), which is incorporated herein by reference in its entirety. Toward this end, integrated PET/CT systems have been developed to facilitate acquisition of both CT and PET data conveniently using a common spatial registration framework. See, e.g. the line of Gemini™ integrated PET/CT scanners (available from Koninklijke Philips Electronics N.V., Eindhoven, the Netherlands). Alternatively, CT and PET data can be acquired by separate CT and PET scanners and relatively spatially registered using a suitable image registration algorithm.

Due to the complexity and extended time frames of cancer therapies, the various therapeutic and monitoring operations are generally performed by different medical personnel at widely varying time intervals. For example, the patient may undergo a chemotherapy session over a period of a few days, during which therapeutic chemical solutions are administered to the patient by nurses, patient physiological parameters such as weight, heart rate, and so forth are recorded at various time intervals, and physicians or other medical personnel examine the patient and record observations or conclusions. Much of these data are entered into the electronic patient record. After completion of the chemotherapy session, the patient has a recovery period during which time the patient does not undergo therapeutic operations, but may undergo monitoring operations such as measurement of physiological parameters. At selected points in the chemotherapy session, the recovery period, or both, the patient may undergo response assessment operations such as a PET/CT scan. These operations may be performed by different medical personnel than those performing the chemotherapy. For example, the PET/CT scan may be performed by a radiological specialist. Moreover, due to the large size of electronic PET and CT image files, the medical imaging data are sometimes stored in a Picture Archiving and Communication System (PACS) that is dedicated to medical images storage and retrieval. The PACS may or may not be electronically linked with the electronic patient record; even if the PACS and patient record databases are linked, information transfer between the two databases is hindered by divergent informational content and data storage formats of the PACS and electronic patient record, respectively.

Although described in terms of PET/CT, similar issues arise for substantially any medical imaging component of a cancer therapy process, such as PET or CT alone, or single photon emission computed tomography (SPECT) imaging acquired using a gamma camera, or magnetic resonance (MR) imaging, or so forth. To summarize, there is a disconnect between the PET/CT or other imaging-based monitoring, and the remainder of the cancer treatment process. This disconnect is present at the electronic information storage level, in that the images stored in the PACS are not well integrated with the remainder of the electronic patient record. The disconnect is also present in at the personnel level, in that radiological specialists who perform medical imaging-based monitoring operations are typically not involved with the remainder of the cancer treatment process. Indeed, in many clinical therapy protocols the PET/CT assessment amounts to a "check box" that is marked off once the patient is scheduled for a PET/CT assessment (or other imaging assessment) and the resulting medical images are received. The images are typically received in printed form, and may be accompanied by a "radiology report" or other documentation prepared by the radiological specialist, usually without knowledge of other non-imaging aspects of the clinical therapy protocol.

Consistency in carrying out clinical therapy protocols also could be improved. For example, some clinical therapy protocols call for the patient to undergo successive PET/CT assessments at different points in the treatment process in order to assess patient response in an ongoing fashion. Since these successive PET/CT assessments are performed on different days that may be separated by weeks or longer, there is generally no assurance that the successive PET/CT assessments will be performed by the same radiological specialist. The different radiological specialists performing the successive imaging assessments may employ different scan protocols or otherwise vary relevant parameters of the PET/CT assessment, which may result in anomalous "differences" between the successive PET/CT assessments that can confuse the doctor or other coordinating medical personnel who use these images in assessing patient response.

The following provides new and improved apparatuses and methods which overcome the above-referenced problems and others.

In accordance with one disclosed aspect, a storage medium stores instructions executable by at least one computer to define an oncology monitoring system including (I) an image analysis module configured to perform oncological monitoring based on medical images of a subject; and (II) a clinical guideline support module configured to (i) display a graphical flow diagram of a clinical therapy protocol including at least one monitoring operation performed by the image analysis module and at least one therapeutic operation not performed by the image analysis module and (ii) interface a user with the graphical flow diagram by performing interfacing operations including at least associating information received by an interfacing operation with a block of the graphical flow diagram selected by the user.

In accordance with another disclosed aspect, an oncology monitoring system comprises: a storage medium as set forth in the immediately preceding paragraph; and a computer executing instructions stored on the storage medium.

In accordance with another disclosed aspect, the oncology monitoring system of the immediately preceding paragraph further comprises: a positron emission tomography (PET) scanner generating the at least one PET image of the subject; and a computed tomography (CT) scanner generating the at least one CT image of the subject; wherein the PET scanner is either separate from the CT scanner or integrated with the CT scanner to define a hybrid PET/CT scanner.

In accordance with another disclosed aspect, an oncology monitoring system comprises: an image analysis module configured to perform an oncological monitoring operation based on images of a subject; and a clinical guideline support module. The clinical guideline support module is configured to: display a graphical flow diagram of a clinical therapy protocol for treating the subject comprising graphical blocks representing therapeutic or monitoring operations of the clinical therapy protocol including at least one monitoring operation performed by the image analysis module; annotate a graphical block of the graphical flow diagram with subject-specific information pertaining to a therapeutic or monitoring operation represented by the graphical block; and display an annotation of a graphical block responsive to selection of the graphical block by a user.

One advantage resides in improved integration of imaging-based monitoring operations with the overall clinical therapy protocol.

Another advantage resides in providing the radiological specialist with relevant non-imaging information that is useful for performing imaging-based monitoring operations such as quantitative image assessment.

Another advantage resides in reduced likelihood of inadvertent variations in successive imaging-based monitoring operations.

Another advantage resides in enhanced workflow efficiency in performing imaging-based monitoring operations in support of a clinical therapy protocol.

FIG. 1 diagrammatically shows a system for monitoring a patient using PET/CT imaging in accordance with a clinical therapy protocol.

Figure 2:
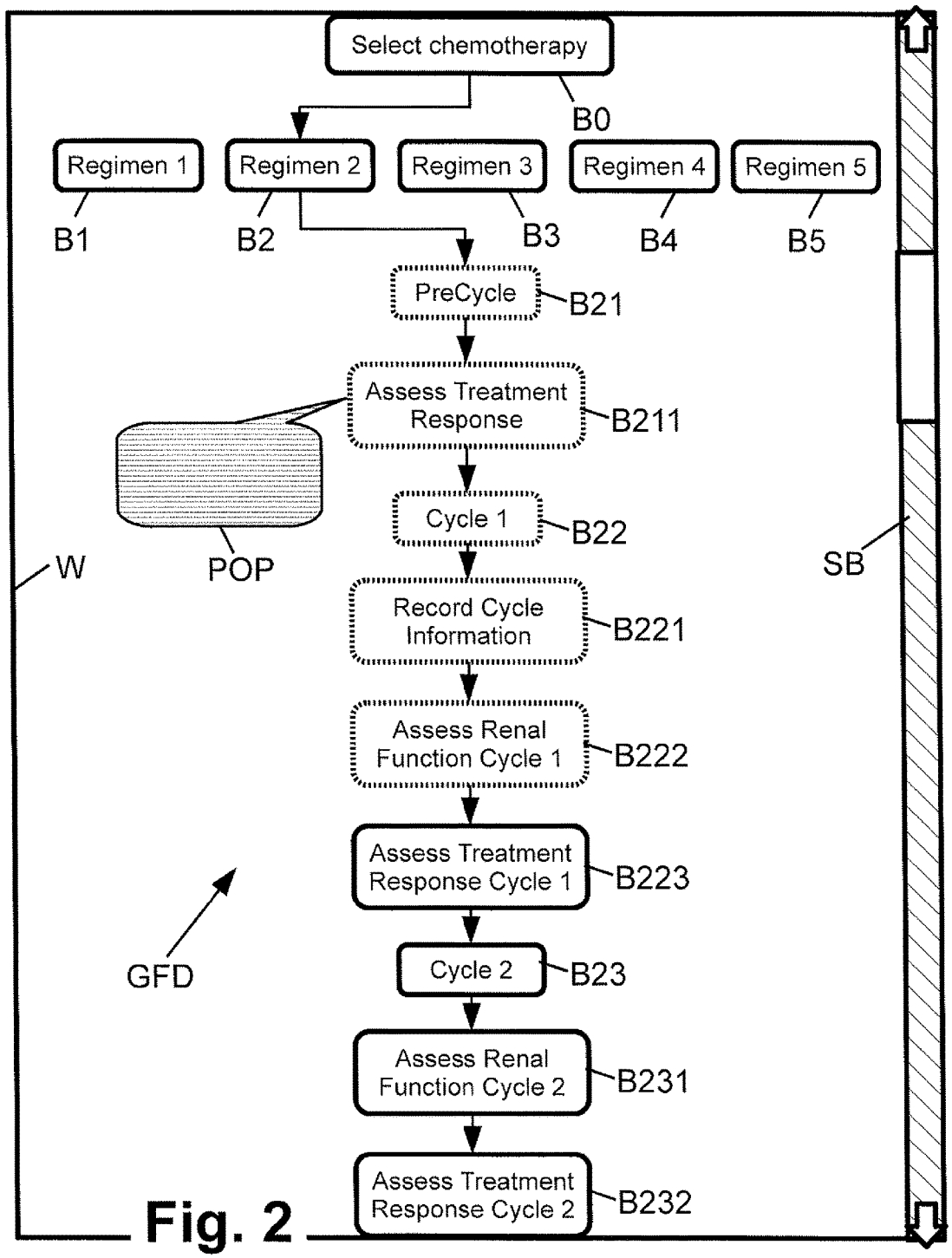

FIG. 2 diagrammatically shows a graphical flow diagram of a clinical therapy protocol generated by and utilized in the system of FIG. 1.

It is recognized herein that a disconnect between the PET/CT or other imaging assessment on the one hand, and the remainder of the cancer therapy process on the other hand, is problematic. For example, to properly interpret the images and assess the change of certain parameters over the course of the therapy, it is useful to reference certain non-image information contained in the electronic patient record, such as information about the course of the overall therapy of the patient, information about the previously applied PET/CT scan protocols, or changes in patient weight. This information is generally not readily available to the radiological specialist.

However, it is also recognized herein that the disconnect between the imaging assessment and the remainder of the cancer therapy process is a consequence of real differences between these two aspects of the treatment process. The performance of PET/CT assessment or other oncological imaging operations is a complex and highly specialized endeavor, and is advantageously performed by a radiological specialist having the requisite specialized knowledge to effectively acquire and analyze the PET and CT or other-modality images. Similarly, other aspects of the cancer treatment process are also highly specialized, and may also be advantageously performed by specialists in the relevant fields. On the electronic information storage level, images are different in kind from most non-image patient data. For example, images are typically represented by large (e.g., megabytes or larger) files containing pixel or voxel information; whereas, nonimaging patient data are typically represented by substantially smaller files containing text, numbers, spreadsheets, or the like. Accordingly, imaging data are not readily integrated with the remainder of the electronic patient record. In recognition of this, the medical arts have developed a bifurcated electronic records topology in which a picture archiving and communication system (PACS) stores medical images separately from (albeit possibly linked with) the remainder of the electronic patient records.

With reference to FIG. 1, these issued are addressed herein by an illustrative PET/CT based therapy monitoring system that includes a clinical guideline support module 10 that provides for authoring, storing, and manipulating clinical therapy protocols. A guideline authoring tool 12 is provided to convert the clinical therapy protocol into a graphical flow diagram (see FIG. 2 for an illustrative example). The resulting graphical flow diagram is stored in a flow diagrams database 14. Typically, the flow diagrams database 14 may store different graphical flow diagrams corresponding to the various different clinical therapy protocols employed at the hospital or other medical facility for treating different types of cancers at different stages of progression or so forth. The guideline authoring tool 12 also enables each graphical flow diagram to be updated as appropriate to reflect changes in the corresponding clinical therapy protocol. Such changes may result from various causes, such as for example: acquisition by the hospital of new equipment suitable for use in the cancer treatment; changes in the clinical therapy protocol recommended by ongoing medical research or past case studies; changes dictated by new or modified government regulations; and so forth.

Each graphical flow diagram stored in the database 14 represents the clinical therapy protocol for a particular type of cancer, particular stage of progression of the cancer, or other therapy protocol classification. However, the graphical flow diagrams stored in the database 14 are generally not patient-specific. As used herein, the term "patient" or "subject" is not intended to denote any particular environment such as a hospital or any particular professional relationship with a doctor or other medical professional. Rather, the terms "patient" or "subject" represent a person undergoing oncological treatment. It is also contemplated for the subject to be an animal undergoing veterinary oncological treatment, treatment as part of a preclinical oncology study, or the like. Although the clinical therapy protocol and corresponding graphical flow diagram are not patient-specific, they may be parameterized based on patient-specific information, for example by specifying a dosage for chemotherapy that is dependent upon patient weight, patient gender, a quantified measure of the extent of the cancer in the patient, or the like. The clinical therapy protocol and corresponding graphical flow diagram may also have divergent flow pathways or optional operations whose selection depends upon patient-specific information, such as patient response to earlier therapy sessions. Other selectable protocol options may accommodate selections or decisions made based on physician preferences or other individualized medical judgments.

With reference to FIG. 2, an illustrative graphical flow diagram GFD is shown. The graphical flow diagram GFD includes: a block BO for selecting chemotherapy, which upon selection causes flow to go to any one of five regimen blocks B1, B2, B3, B4, B5. Each regimen block corresponds to a chemotherapy regimen. If the radiological specialist or other user selects one of the regimen blocks B1, B2, B3, B4, B5, for example by clicking on it using a pointer controlled by a mouse, trackball, or other pointing device, this causes the display of the graphical flow diagram to show the operations that make up the selected chemotherapy regimen. In illustrative FIG. 2, the user has selected chemotherapy regimen #2 by selecting regimen block B2. The selected regimen of the regimen block B2 includes a sequence of operations, namely: a precycle therapeutic operation represented by block B21 followed by a treatment response assessment operation represented by block B211; a first chemotherapy session titled "cycle 1" represented by therapeutic operation block B22 followed by a record cycle operation represented by block B221 followed by a renal function assessment operation represented by block B222 followed by a treatment response assessment represented by a block B223; a second chemotherapy session titled "cycle 2" represented by therapeutic operation block B23 followed by a renal function assessment operation represented by block B231 followed by a treatment response assessment represented by a block B232; and so forth. FIG. 2 illustrates a graphical flow diagram GFD for a chemotherapy treatment; for radiation therapy the therapeutic operation blocks B21, B22, B23, and so forth are suitably replaced by radiation therapy operations, while for brachyotherapy the therapeutic operation blocks B21, B22, B23, and so forth are suitably replaced by radioactive seed implantation operations. It is to be appreciated that FIG. 2 depicts the display of only a portion of the graphical flow diagram in a display window W for exemplary purposes—the radiological specialist or other user suitably operates a vertical scroll bar SB to move up or down to view other portions of the graphical flow diagram in the window W. Horizontal scrolling using a horizontal scroll bar (not shown) is also contemplated, as an alternative to, or in combination with, the illustrated vertical scrolling. If the entire graphical flow diagram fits into the window, then scrolling is optionally omitted.

With continuing reference to FIGS. 1 and 2, the radiological specialist or other user views and interacts with the graphical flow diagram GFD using a flow diagram navigator 20. The available interactions include, for example annotating blocks of the graphical flow diagram with text or the like; selecting a block of the graphical flow diagram GFD to read the annotations associated with the block, and so forth. The annotations input by the user via the flow diagram navigator 20 are suitably stored in a local patient database 22. The subject-specific content contained in the local patient database 22 individualizes or personalizes the graphical flow diagram so as to generate a subject-specific graphical flow diagram. The subject-specific content are retrieved from the local patient database 22 and displayed with the graphical flow diagram GFD whenever the radiologist retrieves and displays the graphical flow diagram GFD for the specific subject.

Blocks of the graphical flow diagram GFD may also be annotated in other ways, such as by automatically populating patient-specific parameters of the graphical flow diagram with information obtained from an electronic patient record 24 by an optional automated populating sub-module 26. The electronic patient record 24 includes information acquired and entered into the record by nurses, doctors, or other medical personnel who interact with the patient, and the recorded information may include, for example: patient weight, heart rate, blood pressure, or other patient parameters measured by medical personnel on an occasional basis; information on the type and stage of the patient's cancer; the chemotherapy regimen administered to the patient; physician's written comments; and so forth. The optional automated populating sub-module 26 extracts relevant information from the electronic patient record 24 and stores it in the local patient database 22, thus reducing the amount of information the radiological specialist manually enters via the flow diagram navigator 20. Where appropriate, the optional automated populating sub-module 26 stores the information extracted from the electronic patient record 24 in the local patient database 22 as annotations to the appropriate node of the protocol. For example, if the electronic patient record 24 identifies the administered chemotherapy regimen, this information is suitably obtained from the electronic patient record 24 by the automated populating sub-module 26, and the sub-module 26 automatically annotates the block B22 corresponding to the first chemotherapy session with relevant information retrieved from the patient record 24, such as the date or dates of administration of the chemotherapy chemical solution or solutions, the administered chemotherapy chemical solution dosages, and so forth.

A color coding scheme or other set of visually distinguishable formats are optionally used to distinguish those operations of the graphical flow diagram that have already been completed from those that have not yet been performed. For example, in illustrative FIG. 2 the operations corresponding to blocks B21, B211, B22, B221, B222 of the graphical flow diagram GFD have already been completed, and accordingly are displayed using dotted line outlines; whereas blocks B223, B23, B231, B232 corresponding to operations that have not yet been completed are displayed using solid line outlines. Alternatively, different colors can be used to distinguish the already-completed blocks from the yet-to-be-completed blocks, or another set of distinguishing formats can be used. In this way, the radiological specialist can readily determine which operations of the clinical therapy protocol have already been performed, and which have yet to be performed.

At certain points in the clinical therapy protocol, the patient is scheduled for PET/CT imaging assessment. For example, in FIG. 2 the next operation to be performed is the treatment response assessment represented by block B223, which includes a PET/CT imaging assessment of the malignant tumor.

Accordingly, the patient arrives at or is delivered to the PET/CT imaging facility (for example, a PET/CT imaging room at a hospital, or an off-site dedicated medical imaging facility associated with the hospital, and so forth). The radiological specialist has medical radiology training, and is qualified to operate a hybrid PET/CT scanner 30 which includes a CT scanner 32 and a PET scanner 34 integrated on a common patient transfer system 36. The hybrid PET/CT scanner 30 is, for example, a Gemini™ integrated PET/CT scanner (available from Koninklijke Philips Electronics N.V., Eindhoven, the Netherlands). Alternatively, PET and CT scanners may be physically separate, for example in separate rooms, in separate buildings, or in physically different locations in a common room (not illustrated). The hybrid PET/CT scanner 30 includes suitable control electronics, portions of which may be variously distributed amongst the gantries 32, 34, stand-alone electronic racks or units, suitably programmed control computers, and so forth. The control electronics are collectively represented in FIG. 1 by a diagrammatic PET/CT controller 38.

The radiological specialist has access to a computer 40 which is preferably located in or near the room containing the hybrid PET/CT scanner 30, and is suitably programmed to implement or embody or operatively communicate with both the clinical guideline support module 10 and an image buffer and analysis module 42 that includes an optional oncology monitoring sub-module 44. The computer 40 optionally also implements or embodies a portion or all of the PET/CT controller 38. The radiologist invokes the image buffer and analysis module 42, which interacts with the PET/CT controller 38 and thence with the hybrid PET/CT scanner 30 to acquire positron emission tomography (PET) and computed tomography (CT) images of the subject.

It is advantageous to ensure that the newly acquired PET and CT images are comparable with images of the subject that have been previously acquired, for example by the imaging-based treatment response assessment corresponding to block B211 which was performed previously. However, the radiological specialist performing the current operation corresponding to block B223 may be different from the radiological specialist of block B211. Even if the same radiological specialist performs the imaging operations of both blocks B211, B223, it may have been days or weeks since the earlier imaging of block B211 was performed, and the radiological specialist may not recall the imaging parameters used in the earlier imaging. Accordingly, the radiological specialist selects block B211 using a pointer controlled by a mouse, trackball, or other pointing device, or using another suitable user selection input device, and responsive to the selection a diagrammatic pop-up window or bubble POP is displayed. The pop-up window or bubble POP displays the annotations associated with block B211 (annotation text not shown in FIG. 2), which preferably include at least the scan parameters used in the earlier PET/CT imaging of block B211. This enables the radiological specialist to ensure that the same scan parameters are used in the current imaging of block B223, thereby ensuring consistency and comparability with the earlier-acquired images. The annotations can be displayed in other formats or places besides the illustrated pop-up window or bubble POP—for example, in some embodiments an annotations window (not shown) that is separate from the illustrated graphical flow diagram window W may be provided for displaying the annotations of the selected block.

The images acquired during the image-based monitoring operation corresponding to block B223 are buffered in the image buffer and analysis module 42, are optionally stored permanently in a picture archiving and communication system (PACS) 46, and are optionally analyzed by the image buffer and analysis module 42.

For the purpose of performing the treatment response assessment represented by block B223, PET and CT images of the cancerous tumor are acquired and are quantitatively analyzed by the optional oncology monitoring sub-module 44 of the image buffer and analysis module 42. For example, the optional oncology monitoring sub-module 44 optionally quantitatively determines a standardized uptake value (SUV) in a selected region of interest around the tumor. To determine patient response over time to ongoing successive therapy treatment sessions, tumor tracking can be performed by comparing the images of the current imaging session (corresponding to treatment assessment block B223 in the illustrative case) with images from previous imaging sessions (such as the previous imaging session represented by already-performed treatment assessment block B211 in the illustrative case) retrieved from the PACS 46. Some suitable tumor tracking processes entail: (1) global rigid registration based on morphological information provided by the CT images; (2) block matching of corresponding volumes of interest performed in the CT images; and (3) SUV-prioritized region growing performed in the PET images. Such tumor tracking processes are described, for example, in Opfer et al., "Automatic lesion tracking for a PET/CT based computer aided cancer therapy monitoring system", in Medical Imaging 2008: Computer-Aided Diagnosis, edited by Maryellen L. Giger and Nico Karssemeijer, Proc. of SPIE Vol. 6915, 691513, (2008), which is incorporated herein by reference in its entirety. Other types of quantitative or qualitative analysis can also be performed, depending upon the nature and stage of the cancer, the imaging modality employed, the parameters to be monitored, and so forth. In general, CT images provide morphological information regarding the structure of the tumor, while PET images provide functional information such as standardized uptake value (SUV) in the vicinity of the tumor. The combination of CT and PET is synergistic—for example, the CT morphology provides information on the physical extent of the tumor, while PET may indicate that a portion of the tumor delineated by CT has necrotized responsive to previous chemotherapy, brachytherapy, or radiation therapy treatment sessions. Some types of quantitative image analysis utilize subject-specific information other than that acquired by the imaging operation, such as patient weight or patient gender. In such analyses, the relevant subject-specific information are suitably retrieved from the local patient database 22 of the clinical guideline support module 10.

The results of the imaging-based monitoring operation performed by the image analysis module 42 are suitably conveyed to the flow diagram navigator 20, which optionally annotates the corresponding block B223 of the graphical flow diagram with the quantitative results (if any) generated by the imaging-based monitoring operation. The flow diagram navigator 20 optionally annotates the block B223 with hyperlinks or other links to the acquired images that are stored in the PACS 46. The flow diagram navigator 20 optionally annotates the block B223 of the graphical flow diagram with scan parameters information regarding the scan parameters used in acquiring the PET and CT images in the monitoring operation corresponding to block B223. Various other types of relevant information are also optionally annotated to the block B223.

If the patient later returns, perhaps days or weeks later, for another PET/CT monitoring operation (for example, corresponding to block B232), the radiological specialist (who may, in general, be the same person as or a different person from the radiological specialist who performed the monitoring operation corresponding to block B223) can readily retrieve the scan parameters used in the last (at that point already-performed) imaging-based monitoring session simply by selecting the block B223 (which at that point will be displayed with a dotted line outline indicating that the block B223 will at that point have already been performed) to cause the annotations of block B223 to be displayed, so as to ensure that the next PET/CT monitoring operation is also performed using the same scan parameters as were used in the previous PET/CT monitoring operations of preceding blocks B211, B223.

The patient-specific data entered into the system by the radiological specialist, or obtained from the electronic patient record 24 by the automated populating sub-module 26, or generated by the imaging analysis module 42, 44, are stored in local patient database 22, so that whenever the patient returns for a successive or follow-up PET/CT assessment, the radiological specialist (who may be the same as or different from the radiological specialist who performed the previous PET/CT assessment) can retrieve the patient data from the local patient database 22 using the displayed graphical flow diagram GFD as a convenient navigational aide. At any time, a radiological specialist can view particular patient data by clicking on corresponding or relevant blocks of the graphical flow diagram representing the clinical therapy protocol. This approach links the radiological specialist with the broader clinical therapy protocol and ensures that the radiological specialist has ready access to relevant non-image information. This, in turn, ensures that the PET/CT assessment adheres to the clinical therapy protocol, and also enables better assessment of the images because relevant non-image data is readily available for use in image assessment.

The disclosed oncology monitoring systems for monitoring a patient using imaging in accordance with a clinical therapy protocol may be physically embodied in various ways. For example, the system of FIG. 1 may be embodied by the computer 40 which executes software defining the clinical guideline support module 10, the image analysis module 42, 44, and optionally a portion or all of the PET/CT controller 38. Typically, this arrangement is advantageous because the computer 40 then provides the radiological specialist with both the clinical therapy protocol information via the clinical guideline support module 10, and the image analysis module 42, 44 for analyzing the PET/CT imaging data. In such embodiments, the computer 40 is typically disposed with or near the hybrid PET/CT scanner 30, for example in the same room with the scanner 30, so that the radiological specialist can reference the graphical flow diagram GFD to retrieve the scan parameters used in the last imaging operation, and can reference non-imaging data stored in the clinical guideline support module 10 in analyzing the PET/CT images. In operation, the clinical guideline support module 10 and the image analysis module 42, 44 are separate software programs executing concurrently on the computer 40. The computer 40 has one or more displays 48 configured to display visual content generated by the image analysis module 42, 44 and visual content generated by the clinical guideline support module 10 simultaneously (for example, in different windows) or in a selectably switched fashion (for example, using an application-switching feature of a multi-tasking operating system of the computer 40).

In the illustrated embodiment, the guideline authoring tool 12 is integrated with the clinical guideline support module 10, and suitably executes on the same computer 40. However, in some settings the radiological specialists who perform the PET/CT image acquisitions may be unqualified to generate the graphical flow diagrams using the authoring tool 12. The authoring of the graphical flow diagram entails holistic knowledge and understanding of the entirety of the clinical therapy protocol, which may be beyond the knowledge of the radiological specialist.

Accordingly, in some embodiments the guideline authoring tool 12 is separate from the remainder of the clinical guideline support module 10. For example, the authoring tool 12 may execute on a computer 50 that is distinct from (albeit possibly networked with) the computer 40 used by the radiological specialist during PET/CT scans. In this variant arrangement, the head of the oncology department, or another specially trained individual, may operate the guideline authoring tool 12 using the computer 50 to generate and/or update the graphical flow diagrams that are then used by the radiological specialists.

The disclosed oncology monitoring systems for monitoring a patient using imaging in accordance with a clinical therapy protocol may also be physically embodied as a storage medium storing instructions executable by at least one computer to define an oncology monitoring system. The storage medium may, for example, include: a magnetic disk or other magnetic storage medium or media; an optical disk or other optical storage medium or media; a flash memory or other electrostatic storage medium or media; a network server storage device; and so forth.

The therapy monitoring system supported by a clinical guideline support module is described herein with reference to the illustrative hybrid PET/CT scanner 30. However, other imaging scanners, systems, or modalities can be employed, such as PET alone, CT alone, a gamma camera configured to perform single photon emission computed tomography (SPECT), a magnetic resonance (MR) imaging system, various combinations or integrated hybrids of such imaging systems, and so forth. In breast cancer therapies, for example, MR is generally a preferred imaging modality for assessing patient response. The skilled artisan can readily replace or adapt the illustrated imaging analysis module 42, 44 to perform oncological monitoring based on images acquired by one or more selected imaging modalities such as SPECT, MR, CT images without corresponding PET images, PET images without corresponding CT images, various combinations thereof, and so forth. Similarly, the clinical guideline support module 10 is readily adapted to display a graphical flow diagram of a clinical therapy protocol including at least one monitoring operation performed by an image analysis module operating on images of modalities other than PET and CT, and to store relevant scan parameters for the selected imaging modality, and so forth. In some contemplated embodiments, the clinical guideline support module 10 is configured to provide support for oncological monitoring based on images acquired by different modalities via suitable graphical flow diagrams constructed using the guideline authoring tool 12 and stored in the flow diagrams database 14. Such a general-purpose clinical guideline support module 10 is useful, for example, in a multi-modality imaging center having multi-modality imaging capability (for example, possessing MR, CT, PET, SPECT, and/or other imaging systems collected at a single site).

The illustrated graphical flow diagram GFD of FIG. 2 is also an illustrative example. Various graphical flow diagrams that graphically embody various clinical therapy protocols are readily constructed using the guideline authoring tool 12 and stored in the flow diagrams database 14 for use with patients undergoing the various clinical therapy protocols. For example, the illustrated five chemotherapy regimens B1, B2, B3, B4, B5 can be replaced by more or fewer regimen options. In constructing a graphical flow diagram for a radiation therapy-based clinical therapy protocol, the illustrated chemotherapy regimens B1, B2, B3, B4, B5 are suitably replaced by one or more radiation therapy regimen options. In a graphical flow diagram for a brachytherapy-based clinical therapy protocol, the illustrated chemotherapy regimens B1, B2, B3, B4, B5 are suitably replaced by one or more brachytherapy regimen options. The clinical therapy protocol may also incorporate other therapeutic operations such as one or more surgical operations, and the selection, naming, and ordering of the various blocks representing therapeutic and monitoring operations can be varied to reflect the specific clinical therapy protocol.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An oncology monitoring system comprising:
   an imaging controller configured to operate an imaging system to acquire medical images of a subject; a computer having a display, the computer configured to:
   perform oncological monitoring operations that operate on the acquired medical images of a subject to analyze a cancerous tumor of the subject;
   display, on the display of the computer, a graphical flow diagram of a chemotherapy, brachytherapy, or radiation therapy protocol for treating the subject, the graphical flow diagram comprising graphical blocks representing, the chemotherapy, brachytherapy, or radiation therapy protocol comprising a plurality of successive chemotherapy, brachytherapy, or radiation therapy sessions comprising a delivery of therapy followed by a recovery period, the graphical flow diagram including:
   (i) therapeutic operations of the chemotherapy, brachytherapy, or radiation therapy protocol that are not performed by the computer and in which chemotherapy, brachytherapy, or radiation therapy treatment is delivered to the subject and
   (ii) oncological monitoring operations of the chemotherapy, brachytherapy, or radiation therapy protocol that are performed by the computer on images of the subject,
   annotate a graphical block of the graphical flow diagram representing an oncological monitoring operation with subject specific information pertaining to scan parameters used in performing the oncological monitoring operation represented by the graphical block and with a result generated by performing the oncological monitoring operation represented by the graphical block, the graphical flow diagram including (i) graphical blocks representing already completed therapeutic or oncological monitoring operations displayed using a first format and (ii) graphical blocks representing not yet completed therapeutic or oncological monitoring operations displayed using a second format that is visually distinguishable from the first format;
   annotate a graphical block of the graphical flow diagram representing a therapeutic operation with subject specific information pertaining to administration to the subject of the therapeutic operation represented by the graphical block, the graphical block transitioning from the first format to the second format upon completion of the therapeutic operation;
   display, on the display of the computer, an annotation of a graphical block responsive to selection of the graphical block by a user;
   control the image controller to operate the imaging system to acquire medical images of the subject using the scan parameters annotated to the identified graphical block to generate a quantitative analysis of the cancerous tumor;
   performing the next graphical block displayed in the second format using the acquired medical images;
   store the annotated imaging assessment blocks in a database;
   retrieve the annotated imaging assessment blocks for a subsequent imagine session of the subject to auto-populate the graphical flow diagram of the chemotherapy, brachytherapy, or radiation therapy protocol for the subject;
   control the image controller to operate the imaging system to acquire medical images of the subject during the subsequent imaging session of the subject using the auto-populated graphical flow diagram;
   annotate the graphical flow diagram with subject-specific information acquired from the medical images acquired during the subsequent imaging session; and
   perform the next graphical block in the annotated graphical flow diagram.

2. The oncology monitoring system as set forth in claim 1, wherein the computer is configured to annotate a graphical block of the graphical flow diagram with subject specific information received from a user pertaining to a therapeutic or oncological monitoring operation represented by the graphical block.

3. The oncology monitoring system as set forth in claim 1, wherein the computer is configured to annotate a graphical block of the graphical flow diagram representing an oncological monitoring operation with quantitative results generated by the represented monitoring operation.

4. The oncology monitoring system as set forth in claim 1, wherein the computer is configured to annotate a graphical block of the graphical flow diagram representing a therapeutic operation not performed by the computer with information pertaining to the therapeutic operation.

5. The oncology monitoring system as set forth in claim 4, wherein the computer is configured to perform an oncological monitoring operation comprising performing quantitative analysis on images of the subject based at least in part on information pertaining to a therapeutic operation not performed by the computer, said information being received via an annotation to a graphical block representing the therapeutic operation.

6. The oncology monitoring system as set forth in claim 1, wherein the computer is configured for operative connection with a positron emission tomography (PET) scanner and with a computed tomography (CT) scanner to control the PET scanner and the CT scanner to acquire the PET and CT images of the subject on which the computer performs oncological monitoring operation.

7. The oncology monitoring system as set forth in claim 1, wherein the computer is further configured to:
perform guideline authoring via which a user constructs the graphical flow diagram of the chemotherapy, brachytherapy, or radiation therapy protocol.

8. The oncology monitoring system as set forth in claim 1, wherein the computer is operatively connected with an imaging system to control the imaging system to acquire the images of the subject on which the computer performs oncological monitoring operations.

9. A method for monitoring a chemotherapy, brachytherapy, or radiation therapy protocol performed on a subject having a cancerous tumor, the method comprising:
using an imaging controller, operate an imaging system to acquire medical images of a subject;
using a computer, retrieving from a database a graphical flow diagram of the chemotherapy, brachytherapy, or radiation therapy protocol including imaging assessment blocks representing oncological monitoring operations performed on the acquired medical images and therapeutic operation blocks representing therapeutic chemotherapy, brachytherapy, or radiation therapy operations, the chemotherapy, brachytherapy, or radiation therapy operations comprising a plurality of successive chemotherapy, brachytherapy, or radiation therapy sessions comprising a delivery of therapy followed by a recovery period, the graphical flow diagram including (i) graphical blocks representing already completed therapeutic or oncological monitoring operations displayed using a first format and (ii) graphical blocks representing not yet completed therapeutic or oncological monitoring operations displayed using a second format that is visually distinguishable from the first format;
using the computer, annotating the graphical flow diagram with subject-specific information specific to the subject having the cancerous tumor;
using the computer, interfacing a user to navigate the graphical flow diagram with the annotated subject-specific information to identify a next imaging assessment block to be performed on the subject the graphical block transitioning from the first format to the second format upon completion of the therapeutic operation;
using the image controller, operate the imaging system to acquire medical images of the subject;
using the computer, performing the next graphical block displayed in the second format using the acquired medical images;
using the computer, annotating the identified imaging assessment block with scan parameters;
using the computer, performing an oncological monitoring operation represented by the identified imaging assessment block on the acquired medical images acquired using the scan parameters annotated to the identified imaging assessment block to generate a quantitative analysis of the cancerous tumor;
using the computer, annotating the identified imaging assessment block with the quantitative analysis of the cancerous tumor;
using the computer, storing the annotated imaging assessment blocks in the database;
using the computer, retrieving the annotated imaging assessment blocks from the database for a subsequent imaging session of the subject to auto-populate the graphical flow diagram of the chemotherapy, brachytherapy, or radiation therapy protocol for the subject;
using the image controller, operate the imaging system to acquire medical images of the subject during the subsequent imaging session of the subject using the auto-populated graphical flow diagram;
using the computer, annotating the graphical flow diagram with subject-specific information acquired from the medical images acquired during the subsequent imaging session; and
using the computer, performing the next graphical block in the annotated graphical flow diagram.

10. The method of claim 9 further comprising:
administering a therapeutic chemotherapy, brachytherapy, or radiation therapy operation to the subject having the cancerous tumor; and
annotating a therapeutic operation block of the graphical flow diagram that represents the administered therapeutic chemotherapy, brachytherapy, or radiation therapy operation with information pertaining to the administering.

* * * * *